United States Patent [19]

Ishiyama et al.

[11] 3,941,770

[45] Mar. 2, 1976

[54] METHOD FOR PURIFYING 3′,5′-CYCLIC-ADENYLIC ACID OR 3′,5′-CYCLIC-DEOXYADENYLIC ACID

[75] Inventors: Jiro Ishiyama, Noda; Tamotsu Yokotsuka, Nagareyama; Motohiko Kato; Nobuyuki Yamaji, both of Noda; Fumihiko Yoshida, Matsudo, all of Japan

[73] Assignee: Kikkoman Shoyu Co., Ltd., Noda, Japan

[22] Filed: Dec. 6, 1973

[21] Appl. No.: 422,566

[30] Foreign Application Priority Data
Dec. 7, 1972  Japan................................ 47-122038

[52] U.S. Cl............................................ 260/211.5 R
[51] Int. Cl.²........................................ C07H 19/20
[58] Field of Search ............................ 260/211.5 R

[56] References Cited
UNITED STATES PATENTS

| | | | |
|---|---|---|---|
| 3,157,636 | 11/1964 | Sanno et al. | 260/211.5 R |
| 3,190,877 | 6/1965 | Ishibashi et al. | 260/211.5 R |
| 3,215,687 | 11/1965 | Tsuchiya et al. | 260/211.5 R |
| 3,287,232 | 11/1966 | Mitsugi et al. | 260/211.5 R |
| 3,457,254 | 7/1969 | Yano et al. | 260/211.5 R |

*Primary Examiner*—Johnnie R. Brown
*Attorney, Agent, or Firm*—Schuyler, Birch, Swindler, McKie & Beckett

[57] ABSTRACT

3′,5′-Cyclic-adenylic acid or 3′,5′-cyclic-deoxadenylic acid can be obtained in a high purity and a high yield by adding a water-soluble organic solvent such as methyl alcohol, ethyl alcohol, n-propyl alcohol, isopropyl alcohol, tert-butyl alcohol, acetone, N,N′-dimethylformamide, dioxane, tetrahydrafuran, ethyleneglycolmonomethylether and the like singly or in combination to an aqueous solution containing as impurities one or more kinds of nucleotides other than 3′,5′-cyclicadenylic acid and 3′,5′-cyclic-deoxyadenylic acid, nucleosides, nucleobases, colored substances, proteins and the like in addition to 3′,5′-cyclic-adenylic acid or 3′, 5′-cyclic-deoxyadenylic acid.

The said 3′,5′-cyclic-adenylic acid or 3′,5′-cyclic-deoxyadenylic acid are useful and valuable as a biochemical reagent.

17 Claims, No Drawings

METHOD FOR PURIFYING 3',5'-CYCLIC-ADENYLIC ACID OR 3',5'-CYCLIC-DEOXYADENYLIC ACID

The present invention relates to a method for purifying 3',5'-cyclic-adenylic acid or 3',5'cyclic-deoxyadenylic acid. More particularly, it relates to a process for purifying 3',5'-cyclic-adenylic acid or 3',5'-cyclic-deoxyadenylic acid from an aqueous solution of 3',5'-cyclic-adenylic acid or 3',5'-cyclic-deoxyadenylic acid, which contains as impurities one or more substances such as nucleotides other than said ones, nucleosides, nucleobases, colored substances, proteins and the like in addition to said 3',5'-cyclic-adenylic acid or 3',5'-cyclic-deoxyadenylic acid.

3',5'-Cyclic-adenylic acid (hereinafter referred to as CAMP) has been known as a participant in various biochemical reactions in vivo and a meditor for a great number of hormones and it is a highly valuable substance. The existence of 3',5'-cyclic-deoxyadenylic acid (hereinafter referred to as DeCAMP) in vivo has been known and it is highly valuable as a biochemical reagent. As stated above, CAMP or DeCAMP is used as a biochemical reagent, therefore, the one having a high purity is required.

CAMP is produced by culturing a microorganism capable of producing CAMP (a microorganism capable of producing CAMP from normal nutrient sources or the one capable of producing CAMP from nucleobases, nucleosides, nucleotides and the like using them as a starting material) in a medium comprising normal nutrient sources or a medium prepared by adding nucleobases, nucleosides, nucleotides and the like to a normal medium (e.g. U.S. Pat. No. 3,630,842); synthesizing by a chemical means using 5'-adenylic acid, 5'-adenosine-diphosphate, 5'-adenosine-triphosphate as a starting material; subjecting 5'-adenosine-triphosphate to an enzymatic treatment using an enzyme, adenylcyclase; or extracting from cells of microorganisms, plants and animals or the like.

DeCAMP is produced by culturing a microorganism capable of producing DeCAMP from deoxyadenosine in a medium containing deoxyadenosine therein; synthesizing by a chemical means using deoxyadenosine as a starting material; decomposing 5'-deoxyadenosine-triphosphate by Baryta water; or subjecting 5'-deoxyadenosine-triphosphate to an enzymatic treatment using the enzyme, adenylcyclase.

The thus obtained CAMP or DeCamp-containing solution, wherein CAMP or DeCAMP exists in the state of free or salt, contains as impurities nucleotides other than CAMP or DeCAMP, nucleosides, nucleobases, colored substances, proteins and the like.

On the occasion of purifying CAMP or DeCAMP in a high purity from CAMP or DeCAMP-containing solutions in which such impurities as the above-mentioned are contained, it is particularly difficult to remove nucleotides other than CAMP or DeCAMP, which are closely related to CAMP or DeCAMP structurally and in physical and chemical properties. When colored substances derived from a medium for fermentation are contained therein, there are some difficulties stated below.

Since said substances often show the quite same behavior as nucleotides other than CAMP or DeCAMP, it makes their removal difficult and prevents CAMP or DeCAMP from crystallizing.

The removal of said substances have been hitherto conducted by an adsorption means using active carbon, or ion exchange resin, a decolorizing resin or the like singly or in combination. A method for purifying CAMP or DeCAMP using such adsorption means as mentioned above has, however, such drawbacks as an industrial means, that the operation is time-consuming and complicate and that the purity of CAMP or DeCAMP obtained is not always sufficient.

There has been known a method for purifying CAMP and DeCAMP by adjusting pH of a CAMP or DeCAMP-containing solution to 1 to 2, adding a CAMP or DeCAMP-insoluble organic solvent such as alcohol, acetone and the like thereto to separate out CAMP or DeCAMP from the solution, however, the purity of CAMP or DeCAMP obtained is extremely low.

An object of the present invention is to provide a method for purifying CAMP or DeCAMP in a high purity and a high yield.

Other objects of the present invention is to provide a highly purified CAMP or DeCAMP.

These and other objects of the prevent invention may become apparent in the following description.

The present inventors have conducted intensively various studies on the method for purifying on an industrial scale CAMP or DeCAMP in a high purity and a high yield with a great easiness from a CAMP or DeCamp-containing aqueous solution in which nucleotides other than CAMP and DeCAMP and other impurities are contained, especially, on a method for removing impurities which are difficult to remove such as, nucleotides other than CAMP or DeCAMP and colored substances derived from a nutrient medium for fermentation, and they have found that impurities such as nucleotides other than CAMP or DeCAMP, colored substances and the like are separated out or precipitated while CAMP or DeCAMP still remain in a dissolved state due to the difference in solubility between CAMP or DeCAMP and impurities such as nucleotides other than CAMP or DeCAMP when an appropriate amount of a water-soluble organic solvent is added to the solution at pH 5 or more. The present invention has been completed based on the above-mentioned finding.

The present invention is concerned with a method for purifying CAMP or DeCAMP which is characterized by obtaining a solution containing CAMP or DeCAMP in a high purity by adjusting an aqueous solution containing as impurities one or more kinds of nucleotides other than said nucleotides, nucleosides, nucleobases, colored substances, proteins and the like in addition to said nucleotides to 5 or more of pH, adding a water-soluble organic solvent in a quantity enough to separate out or precipitate said impurities while maintaining said CAMP or DeCAMP in a state of being dissolved and removing the formed separated materials or precipitates.

The details of the present invention will be given in the following description.

The impurities contained in a CAMP-containing aqueous solution are: nucleotides other than CAMP, (e.g., 3'- or 5'-adenylic acid, 3'- or 5'-inosinic acid, 3'- or 5'-xanthylic acid, 3'- or 5'-guanylic acid, 3'- or 5'-cytidylic acid, 3'- or 5'-uridylic acid and the like), nucleosides (e.g., adenosine, inosine, xanthine and the like), nucleobases (e.g., adenine, hypoxanthine and the like) colored substances (e.g., colored compounds forming from amino acids and sugars with heating alone or together) proteins and the like in the case of fermentation method; nucleotides other than CAMP (e.g., 5'-adenylic acid, 5'-adenosine-diphosphate, 5'-adenosine-triphosphate and the like) and the like in the case of synthetic method; nucleotides other than CAMP (e.g., 5'-adenosine-triphosphate and the like), proteins and the like in the case of enzymatic method; nucleotides other than CAMP (e.g., 5'-adenylic acid, 5'-adenosine-triphosphate, 5'-adenosine-triphosphate and the like), proteins and the like in the case of living body extracting method.

The impurities contained in a DeCAMP-containing aqueous solution are: nucleotides other than DeCAMP (e.g., 5'-deoxyadenylic acid, 5'-deoxyadenosine-diphosphate, 5'-deoxyadenosine-triphosphate and the like) in the case of synthetic method or Baryta-decomposing method; nucleotides other than DeCAMP (e.g., deoxyadenosine-triphosphate and the like), proteins and the like in the case of enzymatic method; nucleotides other than DeCAMP (e.g., deoxyadenylic acid, 3'- or 5'-adenylic acid, 3'- or 5'-guanylic acid, 3'- or 5'-uridylic acid, 3'- or 5'-cytidylic acid and the like), nucleosides (e.g., deoxyadenosine, deoxyinosine and the like), nucleobases (e.g., hypoxanthine and the like), colored substances (e.g., colored compounds forming from amino acids and sugars with heating alone or together), proteins and the like in the case of fermentation method.

The present method is effectively applicable to every solution containing one or more kinds of impurities such as nucleotides other than CAMP or DeCAMP, nucleosides, nucleobases, colored substances, proteins and the like in addition to CAMP or DeCAMP, irrespective of the method for preparing the solution (fermentative methods, synthetic method, enzymatic solution, living body extractive method and the like).

Since the solubility of DeCAMP, when added various kinds of water-soluble organic solvents, in an aqueous solution containing DeCAMP is the same as that of CAMP, the details of present method are given in the following using especially CAMP as an illustrative example.

It is necessary, in the present method, to adjust the pH of an aqueous solution containing CAMP or DeCAMP as well as impurities to 5 or more, preferably 6 – 12, before or after adding a water-soluble organic solvent. In the range that pH is below 5, the aim of the present invention cannot be attained since CAMP or DeCAMP are hardly soluble in water. Illustrative of pH adjusting agents are: sodium hydroxide, potassium hydroxide, ammonium hydroxide, sodium carbonate, sodium bicarbonate, potassium carbonate, potassium bicarbonate, barium hydroxide, calcium hydroxide, hydrochloric acid, sulfuric acid and the like. Additionally, lower organic acids such as formic acid, acetic acid, citric acid and the like may be also employed.

When the pH of an aqueous solution obtained from cultured broth is adjusted to 8 or more, inorganic salts such as magnesium phosphate often separate out from the solution. In such a case, it is preferred to add a water-soluble organic solvent to the solution from which inorganic salts separated out have been removed.

Subsequently, a water-soluble organic solvent is added to the solution containing impurities as well as CAMP or DeCAMP. Illustrative of the solvents are methyl alcohol, ethyl alcohol, n-propyl alcohol, isopropyl alcohol, tert-butyl alcohol, acetone, N,N'-dimethylformamide, dioxane, tetrahydrofuran, ethyleneglycol-monomethylether and the like. These solvents can be used singly or in combination. Among those solvents, acetone, tert.-butyl alcohol, isopropyl alcohol and ethyl alcohol are particularly preferable.

The amount of a water-soluble organic solvent to be added may vary slightly, depending upon the concentration of CAMP or DeCAMP in the solution, the kind of a water-soluble organic solvent, temperature and the like, but, in every case, there is added the amount within the range in which impurities separate out while CAMP or DeCAMP are still dissolved in the solution.

An aqueous CAMP solution containing 5'-adenylic acid (belonging to the group whose solubility to a water-soluble organic solvent is the highest among the impurities) and 5'-inosinic acid, which are the most popular impurities of CAMP-containing solution, was prepared by dissolving CAMP and then a water-soluble organic solvent was added thereto to study in what amount 5'-adenylic acid and 5'-inosinic acid as well as CAMP separated out from the solution. The results thereof are shown as Experimental Examples 1 and 2, respectively.

EXPERIMENTAL EXAMPLE 1

To 1 ml each of an aqueous solution (adjusted to pH 7.5 with 3N NaOH containing CAMP, 5'-adenylic acid and 5'-inosinic acid in the quantities shown in Table 1, respectively, were added from 1 to 50 ml of a water-soluble organic solvent with increasing at the rate of 1 ml at 25°C and the resultants were mixed well. Subsequently, the mixtures in which precipitates were observed after being allowed to stand for 30 minutes [The solution becomes cloudy at the moment that the organic solvent is added, and 50 – 60% of precipitates is usually formed when the cloudy solution is allowed to stand for 30 minutes. The amount of precipitates is a function of temperature and time, however, the content of the remaining substance without separating out in the solution (from which the precipitates are removed) becomes negligible when allowed to stand for 10 – 17 hours even at the same temperature] was subjected to filtration to remove the precipitates. The respective contents of CAMP, 5'-adenylic acid and 5'-inosinic acid in the filtrates were determined by using a paper chromatography to check what substance had separated out. The amounts of the water-soluble organic solvents added, in which each substance began to precipitate, are given in the term of multiple [the amount of a water-soluble organic solvent added to 1 ml of the aqueous solution] in Table 1.

From the industrial viewpoint, the maximum amount of the water-soluble organic solvents to be added was decided to be 50-fold. A 80 : 20 : 2 (volume) mixture of saturated ammonium sulfate: 1 mole/l sodium acetate solution: isopropyl alcohol was employed as a developing solvent for the paper chromatography. It was conducted at 25°C in the manner of ascending chromatography. It was conducted at 25°C in the manner of ascending chromatography. In the case of aqueous solutions containing substances at the rate of 3 mg/ml and 10 mg/ml in Table 1, the determination of the contents of each substance was conducted after the solutions were concentrated up to 1 ml under reduced pressure. The sign "50<" in Table 1 denotes that there was no formation of precipitates even the 50 fold volume of the solvent was added and the terms 5'-AMP and 5'-IMP denote 5'-adenylic acid and 5'-inosinic acid, respectively.

Table 1

| Water-Soluble solvent | Content Nucleotide | 3 mg/ml 5'-CAMP | 5'-AMP | 5'-IMP | 10 mg/ml 5'-CAMP | 5'-AMP | 5'-IMP | 15 mg/l 5'-CAMP | 5'-AMP | 5'-IMP | 100 mg/ml 5'-CAMP | 5'-AMP | 5'-IMP | 250 mg/ml 5'-CAMP | 5'-AMP | 5'-IMP |
|---|---|---|---|---|---|---|---|---|---|---|---|---|---|---|---|---|
| Ethyl alcohol | | 50< | 25 | 13 | 50< | 5 | 4 | 50< | 4 | 3 | 50< | 2 | 1 | 50< | 1 | 1 |
| n-Propyl alcohol | | 50< | 10 | 7 | 50< | 5 | 4 | 50< | 4 | 3 | 9 | 2 | 2 | 8 | 2 | 1 |
| Isopropyl alcohol | | 50< | 6 | 5 | 50< | 4 | 3 | 50< | 3 | 3 | 6 | 2 | 1 | 6 | 1 | 1 |
| tert.-Butyl alcohol | | 50< | 9 | 8 | 50< | 6 | 6 | 50< | 5 | 5 | 4 | 2 | 2 | 4 | 1 | 1 |
| Acetone | | 50< | 5 | 4 | 15 | 4 | 3 | 13 | 3 | 5 | 5 | 2 | 1 | 4 | 1 | 1 |
| Dioxane | | 50< | 14 | 9 | 25< | 8 | 6 | 23< | 7 | 5 | 9 | 4 | 4 | 9 | 3 | 2 |
| Tetrahydrofuran | | 13 | 13 | 8 | 13 | 6 | 4 | 11 | 5 | 3 | 6 | 3 | 2 | 5 | 3 | 2 |

In the case where the substances dissolved in the solution are salts thereof, the amount of a water-soluble organic solvent to be added in order to precipitate each substance agreed well with the one of the water-soluble organic solvent listed in Table 1 when converted the content of the salts to the one of free substance.

The amount of the solvent to be added agreed closely with the one listed in Table 1 even when used nucleotides other than 5'-adenylic acid and 5'-inosinic acid.

A test was conducted to know the range of amount of the solvent to be added in order to precipitate sufficiently impurities such as nucleotides other than CAMP, nucleosides, nucleobases, colored substances, proteins and the like with maintaining CAMP in a state of dissolving, using a cultured broth containing said impurities. The results thereof are given as Experimental Example 2.

EXPERIMENTAL EXAMPLE 2

To a 2.5 mg/ml CAMP-containing cultured broth which had been prepared by culturing a microorganism capable of producing CAMP, Corynebacterium murisepticum No. 7 (FERM-P No. 206, ATCC 21374) in a medium composed of 0.01% of $ZnSO_4·7H_2O$, 0.5% of urea, 0.5% of $(NH_4)_2SO_4$, 1% of $KH_2PO_4$, 1% of $K_2HPO_4$, 1% of polypeptone, 0.5% of yeast extract, 0.7% of sodium inosinate, 5% of glucose, and 1% of $MgSO_4·7H_2O$, with pH 7.5 with shaking at 30°C for 40 hours [In said cultured broth, there were contained as impurities 2.1 mg/ml of 5'-inosinic acid, 0.2 mg/ml of 3'-adenylic acid, 0.3 mg/ml of 5'-adenylic acid, 1.9 mg/ml of inosine, 1.5 mg/ml of hypoxanthine, colored substances (absorbance at 400 m$\mu$: $E_{400}$ = 1.24) and 0.8 mg/ml of proteins], after adjusting the pH of the cultured broth to 10.0 with 40% aqueous sodium hydroxide solution, was added pure CAMP so as to make the content of CAMP the levels shown in Table 2, respectively. The inorganic precipitates (magnesium phosphate) formed when adjusted the broth to pH 10.0 were removed by centrifugation.

Fifty milliliters each of the thus prepared aqueous solutions were poured into a vessel, respectively, and then 1 – 25 fold volume each of water-soluble solvents listed in Table 2 was added (The amount was increased at the rate of 50 ml). The resultant mixture was kept at 5°C for 16 hours to form precipitates and the formed precipitates were removed by filtration to obtain a CAMP-containing solution.

One fifth each of thus obtained solutions was taken out to be concentrated under reduced pressure to remove the water-soluble organic solvent and the contents of various substances in the thus obtained 10 ml of concentrated solution were determined. The contents of CAMP and other nucleotides, nucleosides and nucleobases were determined by two-dimensional ascending paper chromatography at 25°C, using as the first dimensional developing solvent a 10 : 1 : 5 (volume) mixture of isobutyric acid: 1N-acetic acid solution : 1N-ammonium solution and as the second dimensional developing solvent a 80 : 20 : 2 (volume) mixture of saturated ammonium sulfate solution : 1 mole/l sodium acetate solution : isopropylalcohol; the determination of colored substances was conducted by using the absorbance at 400 m$\mu$ ($E_{400}$); and the determination of proteins was conducted by Lowry et. al. method [See Journal of Biological Chemistry 193, 265 (1951)].

The thus obtained CAMP-containing solutions were adjusted to pH 1 – 2 using a 5N hydrochloric acid solution and the resultants were kept at 5°C for 24 hours to form the crystals. The crystals were collected by filtration and the collected precipitates were dried in vacuo to determine the purity of the CAMP crystals and the yield thereof.

The purity of the CAMP crystals was conducted by determining the absorbance at 260 m$\mu$ using spectrophotometer [See Journal of the American Chemical Society 83, 698 (1961)].

Table 2 shows the range of amounts of the solvent to be added; in which about 100% of CAMP remained in said concentrated solution; the amount of remained 5'-inosinic acid was negligible [less than 0.1 mg/ml (unable to determine the one below said level)]; the amounts of remained inosine and hypoxanthine were less than 0.5 mg/ml; the absorbance of the colored substances at 400 m$\mu$ is 0.2 to 0.7; the amount of remained proteins was less than 0.2 mg/ml; the purity of the obtained CAMP crystals was 98% or more and the yield was 70 – 95%.

The CAMP-containing cultured broths obtained in the same manner as mentioned above were adjusted to pH 1 – 2 and then water-soluble organic solvents were added thereto in a quantity enough to precipitate CAMP (e.g., 2 – 25 times the volume). The purities of the obtained CAMP crystals were extremely low such as 50 – 60% and the yields thereof were 70 – 150%.

Table 2

| Water-soluble organic solvent | Content of CAMP | | | | |
|---|---|---|---|---|---|
| | 3 mg/ml | 6 mg/ml | 9 mg/ml | 12 mg/ml | 15 mg/ml |
| Ethyl alcohol | 6–25 | 5–25 | 4–25 | 4–25 | 3–25 |
| n-Propyl alcohol | 6–25 | 5–25 | 4–25 | 4–25 | 3–25 |
| Isopropyl alcohol | 5–15 | 4–10 | 3–8 | 3–7 | 3–7 |
| tert-Butyl alcohol | 5–20 | 4–14 | 3–10 | 3–10 | 3–10 |
| Acetone | 4 | 3 | 3 | 3 | 2 |
| Dioxane | 8–20 | 6–12 | 4–10 | 4–8 | 4–8 |

The procedures of Experimental Examples 1 and 2 were repeated substituting DeCAMP for CAMP and the results thereof are given as Experimental Example 3.

EXPERIMENTAL EXAMPLE 3

1. The procedure of Experimental Example 1 was repeated except that aqueous solutions containing given amounts of DeCAMP and 5'-deoxyadenylic acid (hereinafter referred to as 5'-DeAMP; it belongs to the group whose solubility in the water-soluble organic solvents is the highest among the impurities contained in an aqueous DeCAMP-containing solution) were employed.

The amounts of various water-soluble organic solvents added, in which each substance began to precipitate, are given in the term of multiple [the amount of a water-soluble organic solvent added to 1 ml of the aqueous solution] in Table 3.

Table 3

| Water soluble solvent | Content | 3 mg/ml | | 10 mg/ml | | 15 mg/ml | | 100 mg/ml | | 250 mg/ml | |
|---|---|---|---|---|---|---|---|---|---|---|---|
| | Nucleotide | De-CAMP | 5'-De-AMP | De-CAMP | 5'-De-AMP | De-CAMP | 5'-De-AMP | De-CAMP | 5'-De-AMP | De-CAMP | 5'-De-AMP |
| Ethyl alcohol | | 50< | 25 | 50< | 5 | 50< | 4 | 50< | 2 | 50< | 1 |
| n-Propyl alcohol | | 50< | 10 | 50< | 5 | 50< | 4 | 9 | 2 | 8 | 2 |
| Isopropyl alcohol | | 50< | 6 | 50< | 4 | 50< | 3 | 6 | 2 | 6 | 1 |
| tert.-Butyl alcohol | | 50< | 9 | 50< | 6 | 50< | 5 | 4 | 2 | 4 | 1 |
| Acetone | | 50< | 5 | 15 | 4 | 13 | 3 | 5 | 2 | 4 | 1 |
| Dioxane | | 50< | 14 | 25< | 8 | 23< | 7 | 9 | 4 | 9 | 3 |
| Tetrahydrofuran | | 35 | 13 | 13 | 6 | 11 | 5 | 6 | 3 | 5 | 3 |

2. Brevibacterium liquefaciens (ATCC 14929) was cultured in a medium composed of 20 g/l glucose, 30 g/l DL-alanine, 10 g/l $K_2HPO_4$ and 0.5 g/l $MgSO_4·7H_2O$, of pH 7.0 (adjusted with 3N-KOH) at 30°C for 70 hours with shaking. The resultant cells were collected by centrifugation and the collected cells were suspended in a 100 milli mole/l Tris buffer solution so as to make the absorbance at 660 mμ 20. The thus obtained suspension was subjected to a French-press to destroy the cells and the resultant was used as an enzymatic solution (adenylcyclase).

The said enzymatic solution was admixed at the rate of 1 to 1 with a reaction mixture containing 100 milli mole/l Tris buffer solution (pH 9.0), 10 milli mole/l lithium pyruvate, 20 milli mole/l deoxyadenosinetriphosphate and 100 milli mole/l $MgSO_4$. The resultant admixture was subjected to reaction at 30°C for 10 hours and then the reaction mixture was subjected to heat treatment at 100°C for 10 minutes. The supernatant was obtained by centrifugation.

There were contained 6 milli mole of DeCAMP, 0.8 milli mole of deoxyadenosine-diphosphate and 3.2 milli mole of deoxyadenosine-monophosphate in the 1l of supernatant.

The supernatant was concentrated under reduced pressure to prepare DeCAMP-containing solutions shown in Table 4. The procedure of Experimental Example 2 was repeated substituting the concentrated supernatants for the CAMP-containing solutions to determine the purities of DeCAMP crystals and the yields thereof.

Table 4 shows the range of the amounts of water-soluble organic solvents, in which the purity of the obtained DeCAMP crystals was 93% or more and the yield thereof was 70 to 98%.

Table 4

| Water-soluble organic solvent | Content of DeCamp | | | | |
|---|---|---|---|---|---|
| | 3 mg/ml | 6 mg/ml | 9 mg/ml | 12 mg/ml | 15 mg/ml |
| Ethyl alcohol | 10–25 | 8–25 | 6–25 | 6–25 | 5–25 |
| n-Propyl alcohol | 8–25 | 7–25 | 6–25 | 5–25 | 4–25 |
| Isopropyl | 6–20 | 6–13 | 5–10 | 5–9 | 4–9 |
| tert.-Butyl alcohol | 8–25 | 6–20 | 5–15 | 4–13 | 4–13 |
| Acetone | 5 | 4 | 4 | 4 | 3 |
| Dioxane | 10–25 | 8–15 | 6–13 | 6–10 | 6–10 |

As is clear from the above-mentioned Experimental Examples, impurities can be precipitated or separated while CAMP or DeCAMP still remain without precipitating by choosing an appropriate amount of a water-soluble organic solvent to be added.

In this case, the larger the amount of a water-soluble organic solvent is, the more sufficient the separation or precipitation of impurities is if the amount of the water-soluble organic solvent is within a range that CAMP or DeCAMP still remain without precipitating. From the industrial viewpoints, however, it is preferred to minimize the amount of the water-soluble organic solvent as much as possible. Therefore, the amount of the solvent is decided as the occasion may demand, taking into consideration the above-mentioned viewpoints.

The method according to the present invention, as is clear from the Experimental Examples, can be applicable to any CAMP or DeCAMP containing solution irrespective of the concentration thereof. The content of CAMP or DeCAMP in the solution obtained by fermentation method, synthetic method, living body extraction method and enzymatic method and the like is usually 3 – 15 mg/ml (in the case of salts thereof, they are converted to the content as a free acid), the amount of the solvent to be added can be decided based on the results shown in Tables 1 to 4, especially in the case that the separation is conducted at 5°C or 25°C, while the said amount may very depending upon the temperature.

Even in the case that nucleotides other than CAMP or DeCAMP are contained as impurities in such a small quantity as 0.3 mg/ml, it is possible to remove said impurity until the remaining amount in the solution becomes negligible.

In the case of a cultured broth, the lowest limit for the amounts of organic solvents listed in Tables 2 and 4 except acetone can be lowered to the level next to the lowest one shown in the Tables if there is contained no nucleotides other than CAMP or DeCAMP. That is, the range in the amount of the organic solvent to be added can be expanded.

As stated above, the present method can be applied to the CAMP or DeCAMP and impurities-containing solution without taking into consideration the content of CAMP or DeCAMP. However, it is preferable to supply the present method thereto after concentrating said solution to make the content of CAMP or DeCAMP 100 mg/ml if desired, to thereby the amount of a water-soluble organic solvent to be added can be saved.

The temperature at the time of adding the solvents is usually 0° – 30°C, however, a lower temperature is preferable since the amount of the solvents can be saved.

The impurities are precipitated or separated out sufficiently by allowing the admixture of CAMP or DeCAMP-containing solution and the water-soluble organic solvent to stand for an appropriate time, for example, 3 hours or more.

Especially, in the case of a cultured broth, the colored substances are contained as an impurity. They are hardly removed by conventional means such as the ones using active carbon, decoloring resins and the like since they show the same behaviour as nucleotides other than CAMP and DeCAMP. On the contrary, since the colored substances can be removed as a precipitate according to the present method, the present method is considered to be an extremely effective means.

Even if a cultured broth containing negligible amount of nucleotides other than CAMP and DeCAMP containing no said nucleotides, or the resultant solution obtained by treating said broth with active carbon were employed, it would be impossible to obtain CAMP or DeCAMP in a high yield and a high purity by conventional means because of colored substances. According to the present method, however, it is possible to obtain CAMP or DeCAMP in a high yield and high purity.

In the case that colored substances are contained in extremely large quantities, CAMP or DeCAMP sometimes coprecipitate (CAMP or DeCAMP is not in a state of precipitation) with colored substances when the water-soluble organic solvent is added, thereby the amounts of remaining CAMP or DeCAMP decrease. In such a case, the amounts of remaining CAMP or DeCAMP can be increased by stirring the solution containing deposited impurities at 20° – 50°C for 2 – 3 hours or refluxing it and thereafter allowing it to stand for 30 – 60 minutes or more after impurities have been deposited.

The formed sediments or precipitates of impurities may be removed by conventional means such as filtration, centrifugation and the like. Thus, the solution containing CAMP or DeCAMP in a high purity can be obtained.

When CAMP or DeCAMP is collected from the solution as a crystal which is free form, for example, pH of the solution is adjusted to 3 or less and then the solution is allowed to stand at 0° – 25°C for 6 – 24 hours. Even extremely small amount of nucleosides or nucleobases is contained therein, said substances do not separate out together with CAMP or DeCAMP because of the properties thereof (they are basic or amphoteric). Therefore, CAMP or DeCAMP can be obtained in an extremely high purity.

When pH of the solution is 5 – 7, CAMP or DeCAMP exists as a mixture of free and salt states, and when said pH is more than 7, CAMP or DeCAMP exists in the form of salt. In these cases, CAMP or DeCAMP can be collected as crystal in a state as they are, that is, in a mixture of free and salt forms or in the form of salt. For example, in case where the content of CAMP or DeCAMP in the aqueous solution is 100 mg/ml or more, and a water-soluble organic solvent, such as n-propylalcohol, isopropylalcohol, tert.-butyl alcohol, acetone, dioxane, tetrahydrofuran and the like is used to remove the impurities, the same solvent as used for removal of the impurities is added to the solution in an amount enough to isolate CAMP or DeCAMP therefrom (see Tables 1 and 3) after the removal of the impurities and then the solution is allowed to stand at 0° – 25°C for 16 – 48 hours. Alternatively, for example, the solution is concentrated after the removal of impurities to remove the water-soluble organic solvent so as to make the content of CAMP or DeCAMP 100 mg/ml or more. To this solution, was added a water-soluble organic solvent, such as n-propylalcohol, isopropylalcohol, tert.-butylalcohol, acetone, dioxane, tetrahydrofuran and the like in an amount enough to isolate CAMP or DeCAMP (see Tables 1 and 3) and the resultant solution is allowed to stand at 0° – 25°C for 16 – 48 hours.

As explained in detail, the present method is the one that can be carried out on an industrial scale with a great easiness. Furthermore, the impurities, which have been considered to be the substances difficult to remove from the aqueous solution containing CAMP or DeCAMP, can be removed as precipitates or sediments, thereby, CAMP or DeCAMP can be obtained in a high purity and a high yield. Therefore, it may be concluded that the present method is a very useful means as a method for purifying CAMP or DeCAMP.

The following examples will further illustrate the invention but are not to be considered a limitation thereupon.

EXAMPLE 1

CAMP-containing cultured broth prepared by culturing a CAMP-producing micoorganism, Microbacterium No. 205 (FERM-P No. 106, ATCC 21376), in a medium composed of 5% glucose, 0.5% urea, 0.5% ammonium sulfate, 1% $KH_2PO_4$, 1% $K_2HPO_4$, 1% polypeptone, 0.5% yeast extract, 1% $MgSO_4\cdot 7H_2O$ and 0.5% 5'-insonic acid, of pH 7.5 (adjusted with 3N-KOH) at 30°C for 40 hours with shaking was adjusted to pH 9.5 and the formed inorganic precipitates (magnesium phosphate and the like) were removed by centrifugation to obtain the aqueous solution containing 12 mg/ml CAMP, 1.3 mg/ml 5'-inosinic acid, 1.4 mg/ml inosine, 1.1 mg/ml hypoxanthine, colored substance ($E_{400} = 0.74$) and 2.3 mg/ml proteins.

Subsequently, to each 50 ml of the aqueous solution were added 250 ml (5-fold volume) of various kinds of water-soluble organic solvents. The respective resultant mixtures were kept at 20°C for 16 hours and then the formed sediments (oily materials) were removed by filtration to obtain CAMP-containing solutions.

Each 60 ml of CAMP-containing solutions was taken out and concentrated under reduced pressure, respectively, to remove the organic solvents. The contents of CAMP, 5'-inosinic acid, inosine, hypoxanthine, colored substances and proteins were determined in the same manner as described in Experimental Example 2 using each 10 ml of the thus concentrated solutions. The results obtained are shown in Table 5.

For the sake of confirmation, the contents of 5'-inosinic acid, inosine and hypoxanthine were determined by the same paper chromatography as described in Experimental Example 2, but any of them could not be detected.

Table 6

| Water-soluble organic solvent | Yield of crystalline CAMP (%) | Purity thereof (%) |
|---|---|---|
| Ethyl alcohol | 70 | 99 |
| n-Propyl alcohol | 76 | 98 |
| Isopropyl alcohol | 80 | 98 |
| tert.-Butyl alcohol | 80 | 97 |
| Acetone | 80 | 97 |
| Dioxane | 74 | 98 |

As a reference, said CAMP-containing solution was adjusted to pH 1.5 with 5N-HCl aqueous solution and then 5-folds volume of water-soluble organic solvents listed in Table 7 were added thereto to precipitate CAMP. The results obtained are given in Table 7. The purities thereof were determined in the same manner as described in Experimental Example 2.

Table 7

| Water-soluble organic solvent | Yield of crystalline CAMP (%) | Purity thereof (%) |
|---|---|---|
| Ethyl alcohol | 90 | 51 |
| n-Propyl alcohol | 120 | 50 |
| Isopropyl alcohol | 110 | 55 |
| tert.-Butyl alcohol | 130 | 40 |
| Acetone | 150 | 40 |
| Dioxane | 80 | 55 |

EXAMPLE 2

To 50 ml each of aqueous solutions A-H (adjusted to

Table 5

| Water-soluble organic solvent | CAMP (mg/ml) | 5'-Inosinic acid (mg/ml) | Inosine (mg/ml) | Hypoxanthine (mg/ml) | Colored substances ($E_{400}$) | Proteins (mg/ml) |
|---|---|---|---|---|---|---|
| Ethyl alcohol | 12 | trace | 0.6 | 0.4 | 0.42 | trace |
| n-Propyl alcohol | 12 | " | 0.7 | 0.5 | 0.28 | " |
| Isopropyl alcohol | 12 | " | 0.7 | 0.5 | 0.35 | " |
| tert.-Butyl alcohol | 12 | " | 0.6 | 0.4 | 0.30 | " |
| Acetone | 12 | " | 0.5 | 0.3 | 0.21 | " |
| Dioxane | 12 | " | 0.6 | 0.4 | 0.42 | " |

Each CAMP-containing solution from which sediments had been removed as mentioned above was adjusted to pH 1.5 with 5N-HCl aqueous solution. The resultant solutions were kept at 5°C for 40 hours to crystallize the CAMP Crystals. The formed crystals were collected to dry in vacuo. The yields and purities thereof were determined. The results obtained are shown in Table 6. The determination of the purities was conducted in the same manner as described in Experimental Example 2.

pH 8.0 with 3N-NaOH aqueous solution) containing 5 mg/ml of respective nucleotides therein were added 150 ml (3-folds volume) of acetone and the resultant solutions were kept at 5°C for 16 hours to precipitate impurities. The precipitated impurities were removed by filtration to obtain CAMP-containing solutions.

Forty milliliters each of the solutions were taken out and concentrated under reduced pressure to remove acetone. The contents of respective nucleotides contained in the solution were determined in the same manner as described in Experimental Example 2, using 10 ml each of respective concentrated solutions. The results obtained are given in Table 8.

Table 8

| Group | Nucleotide | Content (mg/ml) | Group | Nucleotide | Content (mg/ml) |
|---|---|---|---|---|---|
| A | 2'-Adenylic acid | trace | E | 2'-Uridylic acid | trace |
|  | 3'-Adenylic acid | " |  | 3'-Uridylic acid | " |
|  | 5'-Adenylic acid | " |  | 5'-Uridylic acid | " |

Table 8-continued

| Group | Nucleotide | Content (mg/ml) | Group | Nucleotide | Content (mg/ml) |
|---|---|---|---|---|---|
|  | CAMP | 5 |  | CAMP | 5 |
| B | 2'-Guanylic acid | trace | F | 2'-Cytidylic acid | trace |
|  | 3'-Guanylic acid | " |  | 3'-Cytidylic acid | " |
|  | 5'-Guanylic acid | " |  | 5'-Cytidylic acid | " |
|  | CAMP | 5 |  | CAMP | 5 |
| C | 2'-Inosinic acid | trace | G | 5'-Adenosine-diphosphate | trace |
|  | 3'-Inosinic acid | " |  | 5'-Adenosine-triphosphate | " |
|  | 5'-Inosinic acid | " |  |  |  |
|  | CAMP | 5 |  | CAMP | 5 |
| D | 2'-Xanthylic acid | trace | H | 5'-Inosine-diphosphate | trace |
|  | 3'-Xanthylic acid | " |  | 5'-Inosine-triphosphate | " |
|  | 5'-Xanthylic acid | " |  |  |  |
|  | CAMP | 5 |  | CAMP | 5 |

EXAMPLE 3

To 50 ml each of the aqueous solution (adjusted to pH 8.0 with 3N-KOH aqueous solution) containing 60 mg/ml CAMP and 60 mg/ml 5'-inosinic acid was added 1 l of the respective organic solvent listed in Table 9. The resultant solutions were kept at 5°C for 24 hours to form precipitates. The formed precipitates were removed by centrifugation to obtain CAMP-containing solutions.

Two hundred 10 milliliters each of the solutions were taken and concentrated under reduced pressure to remove the organic solvent. The contents of CAMP and 5'-inosinic acid were determined in the same manner as described in Experimental Example 2 using 10 ml of respective concentrated solutions. The results obtained are given in Table 9.

Table 9

| Water-soluble organic solvent | CAMP (mg/ml) | 5'-Inosinic acid (mg/ml) |
|---|---|---|
| Methyl alcohol | 60 | trace |
| Ethyleneglycol-monomethyl ether | 60 | " |
| N,N'-Dimethyl-formamide | 60 | " |

EXAMPLE 4

A CAMP-containing cultured broth prepared by culturing a CAMP-producing microorganism, Microbaterium No. 205 (FERM-P No. 106, ATCC 21376), in the same medium as employed in Example 1 at 28°C for 50 hours with shaking was pretreated with active carbon to adsorb CAMP therein. After being washed with water, the adsorbed CAMP was eluated with 50% ethyl alcohol solution containing 1.4% $NH_4OH$ and the eluate was concentrated under reduced pressure to obtain an aqueous solution containing 100.5 mg/ml CAMP, 28 mg/ml inosinic acid, 25 mg/ml hypoxanthine, 21 mg/ml inosine and colored substance ($E_{400} = 8.40$).

To 50 ml of said solution (pH 7.5) was added 150 ml of ethyl alcohol (3-folds volume) and the resultant was kept at 20°C for 20 hours to form precipitates. The formed precipitates were removed by centrifugation to obtain a CAMP-containing solution.

Sixty milliliters of said solution were taken out and concentrated under reduced pressure to remove ethyl alcohol. The contents of CAMP, 5'-inosinic acid, inosine, hypoxanthine and colored substances were determined in the same manner as described in Experimental Example 2 using 10 ml each of thus concentrated solutions. The results obtained are given in Table 10.

Table 10

| CAMP (mg/ml) | 5'-Inosinic acid (mg/ml) | Inosine (mg/ml) | Hypoxanthine (mg/ml) | Colored Substances ($E_{400}$) |
|---|---|---|---|---|
| 50.5 | trace | 0.6 | 0.5 | 0.74 |

The thus obtained solution from which the precipitates had been removed was adjusted to pH 2.0 with 5N-HCl aqueous solution and the resultant was kept at 5°C for 40 hours to crystallize CAMP crystals. The thus formed crystals were treated in the same manner as described in Example 1 to give CAMP crystals having a purity of 99% in a yield of 90%.

As a reference, the said CAMP-containing solution was adjusted to pH 2.0 with 5N-HCl aqueous solution and 3-folds volume of ethyl alcohol was added thereto to crystallize CAMP crystals. Thus, CAMP crystals having a purity of 60% were obtained in a yield of 98%.

EXAMPLE 5

To 50 ml of an aqueous solution adjusted to pH 8.0 with 3N-KOH aqueous solution containing CAMP, 5'-adenylic acid, 5'-adenosine-diphosphate and 5'-adenosine triphosphate at the rate of 5 mg/ml, respectively, was added 250 ml (5-folds volume) of isopropyl alcohol and the resultant solution was kept at 5°C for 16 hours to form precipitates. The formed precipitates were removed by filtration to obtain a CAMP-containing solution.

Sixty milliliters of said solution were taken out and concentrated under reduced pressure to remove isopropyl alcohol until the total volume of the concentrated solution became 10 ml. The contents of CAMP and other nucleotides therein were determined in the same manner as described in Experimental Example 2.

The rate of remaining CAMP was 100% while that of the other nucleotides were negligible.

EXAMPLE 6

To 60 ml of an aqueous solution (pH 8.0, adjusted with 3N-NaOH aqueous solution) containing DeCAMP, 5'-deoxyadenylic acid, 5'-deoxyadenosinediphosphate and 5'-deoxyadenosine-triphosphate at the rate of 10 mg/ml, respectively, was added 360 ml (6-folds volume) of tert.-butyl alcohol and the resultant solution was kept at 5°C for 16 hours to form precipitates. The formed precipitates were removed by filtration to obtain a DeCAMP-containing solution.

Four hundred and twenty milliliters of the said solution were taken out and concentrated under reduced pressure to remove tert.-butyl alcohol. The contents of various nucleotides were determined in the same manner as described in Experimental Example 1, using 10 ml of the thus concentrated solution. Ten mg/ml of DeCAMP were contained while the contents of other nucleotides were negligible.

The thus obtained DeCAMP-containing solution from which the formed precipitates had been removed was adjusted to pH 2.0 with 5N-HCl aqueous solution and the resultant solution was kept at 5°C for 16 hours to crystallize DeCAMP crystals. The crystals were collected by filtration and dried in vacuo to give DeCAMP having a purity of 99.8% in a yield of 98%.

As a reference, said aqueous solution containing DeCAMP, 5'-deoxyadenylic acid, 5'-deoxyadenosinediphosphate and 5'-deoxyadenosine-triphosphate at the rate of 10 mg/ml, respectively, was adjusted to pH 2.0 with 5N-HCl aqueous solution and then 6-folds volume of tert.-butyl alcohol was added to precipitate DeCAMP. Thus, DeCAMP crystal having a purity of 30% were obtained in a yield of 300%.

The purity of DeCAMP was obtained by determining the absorbance at 260 mμ using spectrophotometer similar to that in Experimental Example 2.

What is claimed is:

1. A method for purifying 3', 5'-cyclicadenylic acid or 3', 5'-cyclic-deoxyadenylic acid comprising treating an aqueous solution containing 3', 5'-cyclic-adenylic acid or 3', 5'-cyclic-deoxyadenylic acid and impurities selected from the group consisting of nucleotides other than 3', 5'-cyclic-adenylic acid and 3', 5'-cyclic-deoxyadenylic acid, nucleosides, nucleobases, colored substances, proteins, and mixtures thereof by adjusting the pH to pH 5 or more, and adding a water-soluble organic solvent, said solvent being added in an amount sufficient to separate out or precipitate said impurities at said pH 5 or more while maintaining 3', 5'-cyclic-adenylic acid or 3', 5'-cyclic-deoxyadenylic acid in solution, and removing the separated or precipitated impurities from said solution.

2. A method according to claim 1, wherein the water-soluble organic solvent is at least one member selected from the group consisting of methyl alcohol, ethyl alcohol, n-propyl alcohol, isopropyl alcohol, tert.-butyl alcohol, acetone, N,N'-dimethylformamide, dioxane, tetrahydrofuran and ethyleneglycolmonomethylether.

3. A method according to claim 1, wherein the water-soluble organic solvent is at least one member selected from the group consisting of acetone, tert.-butyl alcohol, isopropyl alcohol and ethyl alcohol.

4. A method according to claim 1, wherein the aqueous solution is adjusted to pH 5 or more with at least one pH-adjusting agent selected from the group consisting of sodium hydroxide, potassium hydroxide, ammonium hydroxide, sodium carbonate, sodium bicarbonate, potassium carbonate, potassium bicarbonate, barium hydroxide and calcium hydroxide.

5. A method according to claim 1, wherein the pH of the aqueous solution is adjusted to 6 – 12.

6. A method according to claim 1, wherein the addition of the water-soluble organic solvent is conducted at a temperature of 0°– 30°C.

7. A method according to claim 1, wherein the formed separated materials or precipitates are removed after being allowed to stand for 3 hours or more.

8. A method according to claim 1, wherein the formed separated materials or precipitates are removed by filtration or centrifugation.

9. A method according to claim 1, wherein the content of 3', 5'-cyclic-adenylic acid or 3', 5'-cyclicdeoxyadenylic acid in the aqueous solution is 100 mg/ml or more.

10. A method according to claim 9, wherein the 3', 5'-cyclic-adenylic acid or 3', 5'-cyclic-deoxyadenylic acid is collected in the form of crystal by adding to the aqueous solution; from which impurities have been previously removed by adding at least one water-soluble organic solvent selected from the group consisting of n-propylalcohol, isopropylalcohol, tert.-butylalcohol, acetone, dioxane and tetrahydrofuran; the same solvent as above in an amount sufficient to isolate 3', 5'-cyclic-adenylic acid or 3', 5'-cyclicdeoxyadenylic acid, allowing the solution to stand at 0°–25°C for 16–48 hours and collecting the formed crystal therefrom.

11. The process of claim 1 wherein said aqueous solution is adjusted to pH 8 or more whereby inorganic salts are separated out or precipitated and said salts are removed from said aqueous solution before addition of said water-soluble organic solvent.

12. The method of claim 1 wherein said impurities comprise colored substances present in large quantities such that 3', 5'-cyclicadenylic acid or 3', 5'-cyclic-deoxyadenylic acid precipitates with said colored substances upon addition of said water-soluble organic solvent, and after addition of said solvent, the concentration of said acids in solution is increased by stirring the solution containing deposited impurities at 20°–50°C. for 2–3 hours or refluxing said solution and thereafter allowing said solution to stand for 30–60 minutes.

13. A method for purifying 3', 5'-cyclic-adenylic acid or 3', 5'-cyclic-deoxyadenylic acid comprising treating an aqueous solution containing 3', 5'-cyclic-adenylic acid or 3', 5'-cyclic-deoxyadenylic acid and impurities selected from the group consisting of nucleotides other than 3', 5'-cyclic-adenylic acid and 3', 5'-cyclicdeoxyadenylic acid, nucleosides, nucleobases, colored substances, proteins and mixtures thereof by adjusting the pH of said solution to pH 5 or more, and adding a water-soluble organic solvent in an amount sufficient to separate out or precipitate said impurities at said pH 5 or more while maintaining 3', 5'-cyclic-adenylic acid or 3', 5'-cyclic-deoxyadenylic acid in solution, removing the separated or precipitated impurities from said solution and thereafter recovering 3', 5'-cyclic-adenylic acid or 3', 5'-cyclic-deoxyadenylic acid from said solution.

14. The method of claim 13 wherein the recovering of said 3', 5'-cyclic-adenylic acid or 3', 5'-cyclic-deoxyadenylic acid is carried out by adjusting the pH of said aqueous solution from which impurities have been separated or precipitated to pH 3 or less, maintaining said aqueous solution of pH 3 or less at a temperature of 0–25°C. for 6–24 hours to crystallize said 3', 5'-cyclicadenylic acid or 3', 5'-cyclic-deoxyadenylic acid from solution and then collecting the crystals.

15. A method according to claim 14, wherein the pH of the solution is adjusted by adding at least one pH-adjusting agent selected from the group consisting of hydrochloric acid, sulfuric acid, formic acid, acetic acid and citric acid.

16. A method for purifying 3', 5'-cyclic-adenylic acid or 3', 5'-cyclic-deoxyadenylic acid consisting essentially of adjusting an aqueous solution containing 3', 5'-cyclic-adenylic acid or 3', 5'-cyclicdeoxyadenylic acid, at least one impurity selected from the group consisting of proteins and nucleotides other than 3', 5'-cyclic-adenylic acid and 3', 5'-cyclic-deoxyadenylic acid and at least one impurity selected from the group consisting of nucleosides, nucleobases and colored substances to pH 5–12, adding at least one water-soluble organic solvent selected from the group consisting of methyl alcohol, ethyl alcohol, n-propyl alcohol, isopropyl alcohol, tert.-butyl alcohol, acetone, n, n'-dimethylformamide, dioxane, tetrahydrofuran and ethyleneglycolmonomethylether in an amount sufficient to separate or precipitate said impurities with maintaining said 3', 5'-cyclic-adenylic acid or 3', 5'-cyclic-deoxyadenylic acid in solution, separating the formed separated materials or precipitates therefrom, adjusting the pH of the aqueous solution to 3 or less and then collecting the crystallized 3', 5'-cyclic-adenylic acid or 3', 5'-cyclic-deoxyadenylic acid from the solution.

17. A method according to claim 16 wherein the aqueous solution, the pH of which is adjusted to 3 or less, is kept at a temperature of 0°–25°C. for 6–24 hours.

* * * * *